United States Patent

Fang et al.

[11] Patent Number: 6,143,891
[45] Date of Patent: *Nov. 7, 2000

[54] METHOD FOR PREPARING CAMPTOTHECIN DERIVATIVES

[75] Inventors: Francis Gerard Fang, Andover, Mass.; Shiping Xie, Cary, N.C.

[73] Assignee: Glaxo Wellcome Inc., Research Triangle Park, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 09/068,185

[22] PCT Filed: Nov. 1, 1996

[86] PCT No.: PCT/US96/17574

§ 371 Date: May 14, 1998

§ 102(e) Date: May 14, 1998

[87] PCT Pub. No.: WO97/16454

PCT Pub. Date: May 9, 1997

Related U.S. Application Data

[60] Provisional application No. 60/006,138, Nov. 2, 1995.
[51] Int. Cl.⁷ ................................................ C07D 491/22
[52] U.S. Cl. ............................. 544/361; 546/41; 546/48
[58] Field of Search ............................. 546/41, 48, 116; 544/361

[56] References Cited

FOREIGN PATENT DOCUMENTS

WO92/07856  5/1992  WIPO .
WO93/16698  9/1993  WIPO .

OTHER PUBLICATIONS

Krohn et al., Chemical Abstracts, vol. 83, abstract 193573, 1975.
Herzberg, R.P., *Journal of Medicinal Chemistry*, vol. 32, No. 3, 1989, pp. 715–720, "Modification of the Hydroxy Lactone Ring of Camptothecin".
*Chemical Abstracts Registry Handbook Number Section*, 1992, pp. 4277ru, "See Compound with rn=143490-55-5".
S. Sawada, et al., *Chemical Abstracts*, vol. 117, No. 17, 1992, pp. 882, "Preparation of Camptothecin Derivatives as Anti-tumor Agents".

Fang, F.G. et al., *Journal of Organic Chemistry*, vol. 59, No. 21, 1994, pp. 6142–6143, "Catalytic Ennantioselective Synthesis of 20(S)–Camptothecin: A Practical Application of the Sharpless Asymmetric Dihydroxylation Reaction".

Krohn, K. et al., *Chemische Berichte*, vol. 108, 1975, pp. 3030–3042, "Alkylierung Von Campothecin–Vorstufen".

Primary Examiner—Richard L. Raymond
Attorney, Agent, or Firm—John L. Lemanowicz

[57] ABSTRACT

The present invention relates to a process for preparing camptothecin and camptothecin analogs of Formula (I) from compounds of Formula (II) and to novel intermediates useful in their preparation,

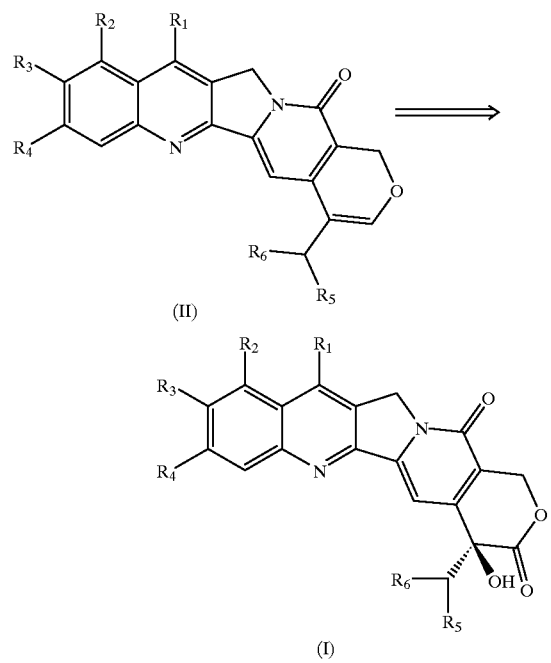

wherein $R_1$ to $R_6$ represent various substituents.

8 Claims, No Drawings

METHOD FOR PREPARING CAMPTOTHECIN DERIVATIVES

This application is filed pursuant to 35 U.S.C. § 371 as a United States National Phase Application of International Application No. PCT/US96/17574 filed Nov. 1, 1996 which claims priority from U.S. Provisional 60/006,138 filed Nov. 2, 1995.

FIELD OF THE INVENTION

The present invention relates to a method of preparing camptothecin and camptothecin analogs employing chemical compounds that are useful as intermediates and to processes for the preparation of the intermediates.

BACKGROUND OF THE INVENTION

Camptothecin is a naturally occurring compound, found in *Camptotheca acuminata*. Camptothecin and camptothecin analogs have been found to have anti-leukemic and anti-tumor properties.

Camptothecin and camptothecin analogs can be synthesized using processes described in U.S. Pat. No. 4,894,456 to Wall et al. issued Jan. 16, 1990; U.S. Pat. No. 4,399,282 to Miyasaka, et al. issued Aug. 16, 1983; U.S. Pat. No. 4,399,276 to Miyasaka, et al. issued Aug. 16, 1983; U.S. Pat. No. 4,943,579 to Vishnuvajjala, et al. issued Jul. 24, 1990; European Patent Application 0 321 122 A2 filed by SmithKline Becham Corporation, and published Jun. 21, 1989; U.S. Pat. No. 4,473,692 to Miyasaka, et al. issued Sep. 25, 1984; European Patent application No. 0 325 247 A2 filed by Kabushiki Kaisha Yakult Honsh, and published Jul. 26, 1989; European Patent application 0 556 585 A2 filed by Takeda Chemical Industries, and published Aug. 25, 1993; U.S. Pat. No. 4,981,968 to Wall, et al. issued Jan. 1, 1991; U.S. Pat. No. 5,049,668 to Wall, et al. issued Sep. 17, 1991; U.S. Pat. No. 5,162,532 to Comins, et al.; issued Nov. 10, 1992; U.S. Pat. No. 5,180,722 to Wall, et al. issued Jan. 19, 1993 and European Patent application 0 540 099 A1, filed by Glaxo Inc., and published May 5, 1993.

Previous methods used in the preparation of camptothecin and camptothecin analogs employ resolutions or chiral auxiliaries to obtain enantiomerically enriched intermediates. A problem with these methods is that a resolution necessitates discarding half of the racemic material and a chiral auxiliary requires utilizing stoichiometric amounts of a chiral subunit to stereoselectively install the chiral center.

A method which uses a process of catalytic asymmetric induction is described in U.S. patent application Ser. No. 08/237,081 and Fang et al., Journal of Organic Chemistry, 59(21), 6142–6143 (1994). One potential problem with such prior methods is that some of the chirally specific intermediates themselves may exhibit cell toxicity. Furthermore, the final step of the synthesis described in U.S. patent application Ser. No. 08/237,081, now U.S. Pat. No. 5,491,237, requires the use of a palladium catalyst which must subsequently be removed from the final drug substance by multiple recrystallizations. The potent cytotoxicity of camptothecin and some of its analogs requires that stringent safeguards be imposed during all the later steps of manufacturing to protect production personnel and the environment. Such safeguards increase the complexity and cost of manufacturing and handling camptothecin and its analogs.

An object of the present invention is a method for the preparation of camptothecin and its analogs wherein the chirality at the 20 position is not introduced until the penultimate manufacturing step. This would reduce the risk of accidental contamination of the environment and injury to the production worker, and hence, reduces the need for stringent safeguards, since handling and storage of highly biologically active material is minimized.

SUMMARY OF THE INVENTION

The present invention provides a method of preparing compounds of Formula (I) which comprises oxidizing compounds of Formula (II)

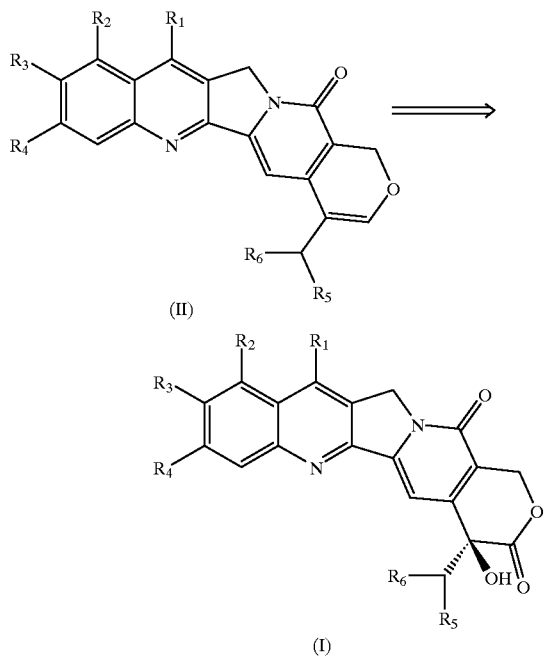

wherein:

$R_1$ and $R_2$, which may be the same or different, are independently selected from hydrogen, lower alkyl, $(C_{3-7})$cycloalkyl, $(C_{3-7})$cycloalkyl lower alkyl, lower alkenyl, hydroxy lower alkyl, or alkoxy alkyl, or (—$CH_2NR_7R_8$), wherein:

i) $R_7$ and $R_8$, which may be the same or different, are independently selected from hydrogen, lower alkyl, $(C_{3-7})$ cycloalkyl, $(C_{3-7})$ cycloalkyl lower alkyl, lower alkenyl, hydroxy lower alkyl, or lower alkoxy lower alkyl; or ii) $R_7$ represents hyrogen, lower alkyl, $(C_{3-7})$ cycloalkyl, $(C_{3-7})$ cycloalkyl lower alkyl, lower alkenyl, hydroxy lower alkyl, or lower alkoxy lower alkyl, and $R_8$ represents —$COR_9$, wherein:

$R_9$ represents hydrogen, lower alkyl, perhalo-lower alkyl, $(C_{3-7})$cycloalkyl, $(C_{3-7})$ cycloalkyl lower alkyl, lower alkenyl, hydroxy lower alkyl, lower alkoxy, lower alkoxy lower alkyl; or iii) $R_7$ represents hydrogen or lower alkyl; and $R_8$ represents diphenyl-methyl or —$(CH_2)_tAr$ wherein:

t is 0 to 5 and

Ar represents phenyl, furyl, pyridyl, N-methylpyrrolyl, imidazolyl optionally subsituted with one or more substituents selected from hydroxy, methyl, halogen, and amino; or iv) $R_7$ and $R_8$ taken together with the linking nitrogen form a staturated 3 to 7 atom heterocyclic group of formula (IA)

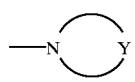

(IA)

wherein:
Y represents O, S, SO, $SO_2$, $CH_2$ or $NR_{10}$,
wherein:
$R_{10}$ represents hydrogen, lower alkyl, perhalo lower alkyl, aryl, aryl substituted with one or more substituents selected from lower alkyl, lower alkoxy, halogen, nitro, amino, lower alkyl amino, perhalo-lower alkyl, hydroxy lower alkyl, lower alkoxy lower alkyl groups or
—$COR_{11}$,
wherein:
$R_{11}$ represents hydrogen, lower alkyl, perhalo-lower alkyl, lower alkoxy, aryl, aryl substituted with one or more substituents selected from lower alkyl, perhalo-lower alkyl, hydroxy lower alkyl, lower alkoxy lower alkyl groups; or $R_3$ and $R_4$ are independently selected from hydrogen, lower alkyl, ($C_{3-7}$)cycloalkyl, ($C_{3-7}$)cycloalkyl lower alkyl, lower alkenyl, hydroxy lower alkyl, or alkoxy alkyl; or $R_3$ and $R_4$ taken together form a saturated 5 to 6 atom heterocyclic group of formula (IB)

(IB)

wherein,
n represents the integer 1 or 2; or
$R_3$ represents —$OCONR_{12}R_{13}$,
wherein,
$R_{12}$ and $R_{13}$, which may be the same or different, are independently selected from hydrogen, a substituted or unsubstituted alkyl group with 1–4 carbon atoms or a substituted or unsubstituted carbocyclic or heterocyclic group, with the proviso that when both $R_{12}$ and $R_{13}$ are substituted or unsubstituted alkyl groups, they may be combined together with the nitrogen atom, to which they are bonded, to form a heterocyclic ring which may be interrupted with —O—, —S— and/or >N—$R_{14}$ in which $R_{14}$ is hydrogen, a substituted or unsubstituted alkyl group with 1–4 carbon atoms or a substituted or unsubstituted phenyl group, and $R_5$ represents hydrogen or alkyl, particularly methyl, and
$R_6$ represents hydrogen or alkyl, particularly hydrogen, and
pharmaceutically acceptable salts thereof.

The present invention further provides a method of preparing compounds of Formula (I) which comprises dihydroxylating a compound of Formula (II) and subsequent oxidation to yield a compound of Formula (I).

In addition to a method of preparing compounds of Formula (I) from compounds of Formula (II), other aspects of the invention include the compounds of Formula (II) and various intermediates useful in the formation of compounds of Formula (I) and (II). Other aspects and advantages of the present invention will become apparent from a review of the detailed description below.

DETAILED DESCRIPTION OF THE INVENTION

As used herein, the term "loweralkyl" means, a linear or branched alkyl group with 1–8, preferably 1–4 carbon atoms, such as, methyl, ethyl, propyl, isopropyl, n-butyl, tert-butyl, hexyl and octyl. This definition also applies to a loweralkyl moiety in the loweralkoxy, loweralkylthio, and di(loweralkyl)amino groups. Thus, examples of loweralkoxy groups are methoxy, ethoxy, propoxy, sec-butoxy, and isohexoxy: examples of loweralkylthio groups are methylthio, ethylthio, tert-butylthio, and hexylthio, and examples of di(loweralkyl)amino groups are dimethylamino, diethylamino, diisopropylamino, di(n-butyl)amino, and dipentylamino.

The terms "halo" and "halogen" as used herein refer to a substitutent which may be fluoro, chloro, bromo, or iodo. The term "triflate" as used herein refers to trifluoromethanesulfonate. The designation "C" as used herein means centigrade. The term "ambient temperature" as used herein means from about 20° C. to about 30° C.

Compounds of the present invention may have 1 or more asymmetric carbon atoms that form enantiomeric arrangements, i.e., "R" and "S" configurations. The present invention includes all enantiomeric forms and any combinations of these forms. For simplicity, where no specific configuration is depicted in the structural formulas, it is to be understood that both enantiomeric forms and mixtures thereof are represented. Unless noted otherwise, the nomenclature convention, "(R)" and "(S)" denote essentially optically pure R and S enantiomers, respectively.

Also included in the present invention are other forms of the compounds including: solvates, hydrates, various polymorphs and the like.

Acceptable salts include, but are not limited to, salts with inorganic acids and bases such as hydrochloride, sulfate, phosphate, diphosphate, hydrobromide and nitrate or salts with organic acids such as acetate, malate, maleate, fumarate, tartrate, succinate, citrate, lactate, methanesulfonate, p-toluenesulfonate, palmoate, salicylate, oxalic and stearate. For further examples of acceptable salts see, "Pharmaceutical Salts," *J. Pharm. Sci.*, 66(1), 1 (1977).

One aspect of the present invention provides a method for preparing compounds of Formula (III);

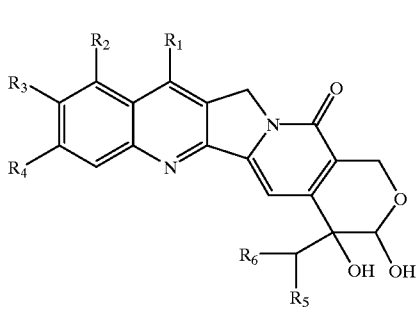

(III)

which comprises dihydroxylating a compound of Formula (II),

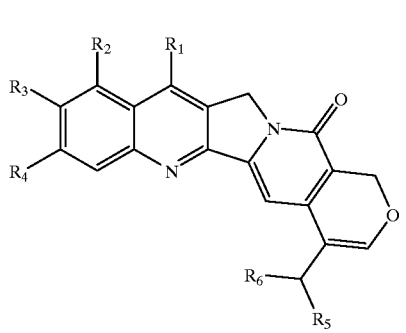

(II)

using a catalytic asymmetric dihydroxylation reaction. Typically, the reaction may be carried out in the presence of an osmium catalyst (e.g., potassium osmate (VI) dihydrate, osmium(III) chloride hydrate or osmium tetroxide), a chiral tertiary amine catalyst (e.g., derivatives of the cinchona alkaloids such as hydroquinidine 1,4-phthalazinediyl diether), an oxidizing reagent (e.g., potassium ferricyanide (III), hydrogen peroxide, N-methylmorpholine N-oxide, or electricity), and a primary amide (e.g., methanesulfonamide) under basic conditions (e.g. potassium carbonate) in an aqueous mixture containing a polar protic solvent (e.g., t-butanol, i-propanol, or n-propanol). The reaction may be carried out at a temperature of between about 0° C. to about 30° C. for about 12 to about 48 hours. Acceptable variations on these conditions are described in the literature on related catalytic asymmetric dihydroxylation reactions, e.g., K. B. Sharpless et al., *J. Org. Chem.* 58, 3785–3786 (1993).

Alternatively the compound of Formula II is oxidized to a compound of Formula III in an achiral dihydroxylation reaction to yield a racemic cis-diol which is then resolved enzymatically to give the enantiomerically enriched compound of Formula III. Descriptions of achiral dihyroxylations are provided by Larock, *Comprehensive Organic Transformations*, 493–496 (1989). The resolution reaction may be carried out in the presence of an acylating enzyme such as pancreatic lipases, *Pseudomonas fluorenscens* lipases, *C. Cylindracea* lipases, *Chromobacterium viscosum* lipases and *Aspergillus niger* lipases in the presence of an acylating agent such as vinyl acetate at a temperature of between about 0° C. to ambient temperature for about 2 to about 48 hours. Variations on these conditions will be apparent from A. Klibanov, Asymmetric Transformations Catalyzed by Enzymes in Organic Solvents, *Acc. Chem. Res.* 23, 114–120 (1990).

Compounds of Formula (II) may be prepared by cyclizing a compound of Formula (IV),

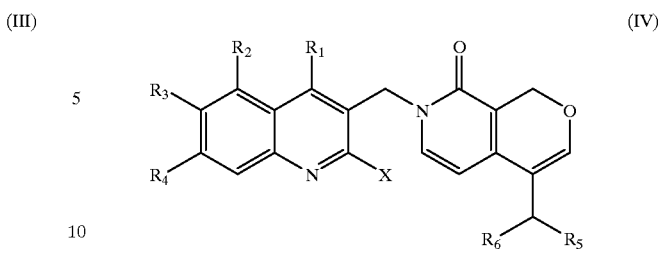

(IV)

wherein

X represents triflate or halo, particularly chloro-, bromo-, and iodo-.

The compounds of Formula (IV) may be cyclized by an intramolecular Heck reaction. The reaction may be carried out in the presence of a palladium catalyst (e.g., palladium (II) acetate) under basic conditions in a polar aprotic solvent (e.g. acetonitrile or N,N-dimethylformamide) or a polar protic solvent (e.g., n-propanol, i-propanol, or t-butanol). A phase transfer catalyst such as a tetraalkylammonium halide salt (eg., tetrabutylammonium chloride, tetrabutylammonium bromide, or tetrabutylammonium iodide) may be included when a polar aprotic solvent is used. Preferably, a ligand for the palladium catalyst may also be included such as a triphenylphosphine, tri-o-tolylphosphine, tri-m-tolylphosphine, or tri-p-tolylphosphine. The reaction may be carried out in an inert atmosphere, such as under nitrogen or argon gas in a suitable reaction vessel equipped with mechanical stirrer and water-cooled condenser. The reaction mixture may be heated to a temperature between about 50° to about 110° C. for about 1 to about 48 hours. Variations on these conditions are described in the literature on the Heck reaction, e.g., R. Grigg et al., *Tetrahedron* 46, 4003–4008 (1990).

The compounds of Formula (IV) may be prepared by condensing compounds of Formula (V) and Formula (VI).

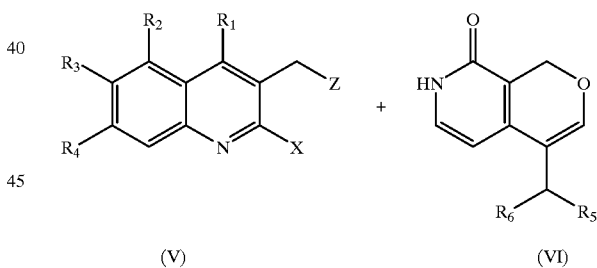

(V)    (VI)

wherein,

X represents triflate or halo particularly chloro-, bromo-, and iodo- and Z represents a suitable leaving group such as chloro-, bromo- and, iodo- or $OR_{15}$, wherein $R_{15}$ represents triflate, mesylate, or tosylate, or particularly H.

In the case wherein Z represents hydroxy, the condensation reaction is carried out in an aprotic solvent, e.g., methylene chloride, in the presence of a trialkyl- or triarylphosphine, e.g., triphenylphosphine, and a dialkyl azodicarboxylate, e.g., diethyl azodicarboxylate, at a temperature between about 0° C. to about 50° C. for about 0.5 to 4 hours. Further variations on the above conditions will be apparent from the literature on the Mitsunobu reaction, e.g., O. Mitsunobu, *Synthesis,* 1, (1981).

When Z represents halo, triflate, mesylate, or tosylate, the condensation reaction is carried out in a polar aprotic solvent such as acetonitrile or N,N-dimethylformamide, or a polar protic solvent such as i-propanol or t-butanol, in the presence of a base, e.g., potassium t-butoxide, at a temperature between about 25° C. to about 100° C. for about 1 to 24 hours to yield compounds of Formula (IV). Variations on the above conditions are described in U.S. Pat. No. 5,254,690 to Comins et al. issued Oct. 19, 1993 and incorporated herein by reference.

Compounds of Formula (VI) may be prepared from compounds of Formula (VII),

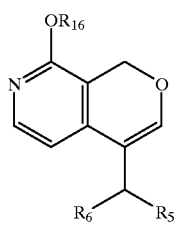

wherein, $R_{16}$ represents alkyl, particularly methyl.

The dealkylation reaction may be carried out in a polar aprotic solvent, e.g. acetonitrile, in the presence of a suitable dealkylating reagent, e.g., a trialkylsilyl iodide, at a temperature between about 0° C. and 100° C. for about 1–12 hours. The trialkylsilyl iodide may be generated in situ by combining a trialkylsilyl halide, e.g., trimethylsilyl chloride, and an alkali metal iodide, e.g., sodium iodide.

Alternatively the dealkylation reaction may be carried out in a polar, protic solvent, e.g., water or ethanol, in the presence of a strong acid, e.g., hydrochloric acid at a temperature between about 0° C. and 100° C. for about 1 to 24 hours to yield the compound of Formula (VI).

The starting materials, the compounds of Formula (V) and Formula (VII), are described in U.S. patent application Ser. No. 08/237,081, now U.S. Pat. No. 5,491,237, Fang et al., Journal of Organic Chemistry, 59(21), 6142–6153 (1994), PCT/US95/05425, and PCT/US95/05427.

The compounds of Formula (III) may be oxidized to yield a compound of Formula (I).

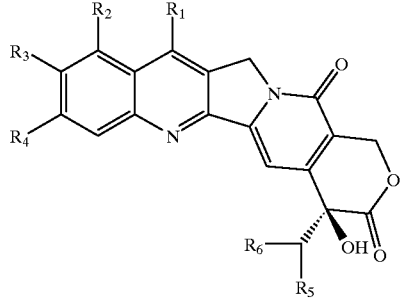

The oxidation reaction may be carried out in a suitable solvent, e.g., methylene chloride, in the presence of an oxidizing agent, e.g., dimethylsulfoxide, an activating reagent, e.g., oxalyl chloride, and a base, e.g., triethylamine, at a temperature between about −78° C. and −20° C. for about 0.1 to about 1 hours to yield a compound of Formula (I). Further variations on these conditions will be apparent from the literature on activated sulfur-based oxidants, e.g., Mancuso and Swern, *Synthesis,* 165–185 (1981) and March, J., *Advanced Organic Chemistry,* 3rd edition, John Wiley & Sons, New York (1985), pp. 1057–1060, 1081–1082.

Thus, progressing compounds of Formula (V) and (VI) to compounds of Formula (I) through the intermediate compounds of Formula (IV), (II), and (III) is schematically represented by the following scheme:

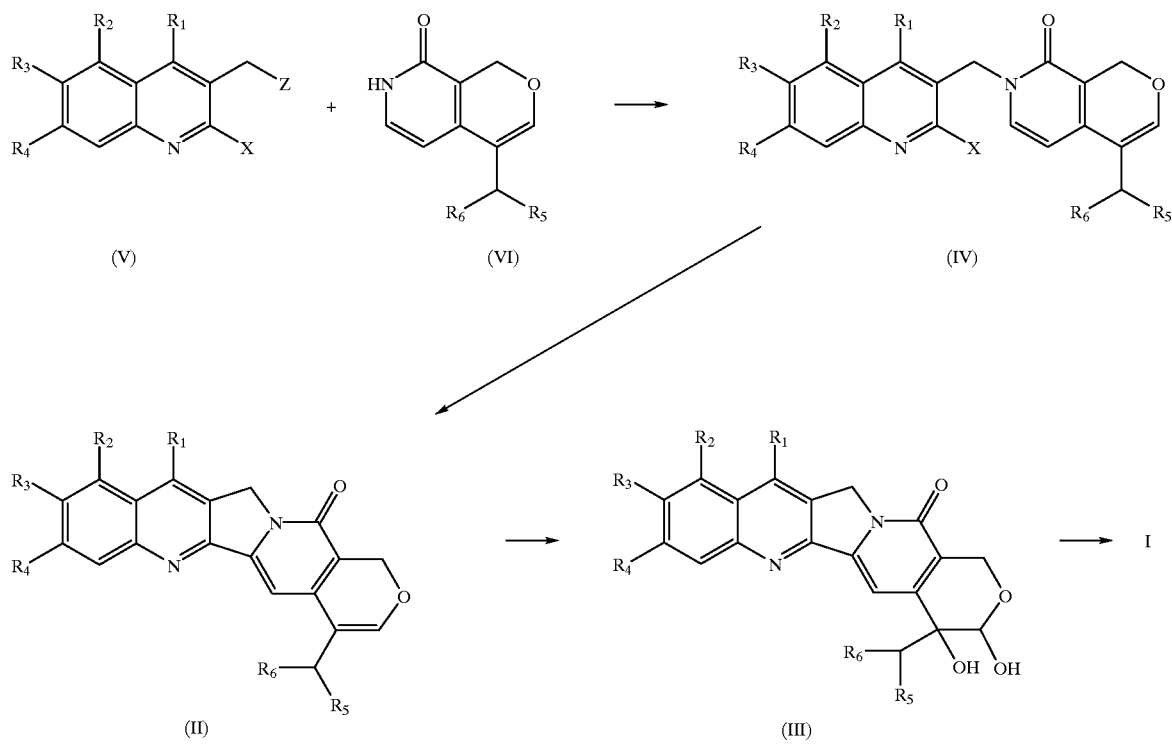

A further aspect of the invention are the novel compounds of Formula (II), (III), (IV), and (VI).

The compounds of Formula (II), (III), (IV), (V), (VI), and (VII) are useful as intermediates in the preparation of camptothecin and camptothecin analogs, e.g. compounds of Formula (I), and those described in European Patent application 0 540 099 A1, filed by Glaxo Inc., and published May 5, 1993 and incorporated herein by reference.

A typical preparation of a camptothecin derivative of Formula (I) using intermediate compounds of Formula (II), (III), (IV), (V), (VI), and (VII) is exemplified herein.

EXAMPLES

The following examples illustrate various aspects of the present invention, but should not be construed as limitations. The symbols, conventions and nomenclature not specifically defined below are consistent with those used in the contemporary chemical literature, for example the *Journal of the American Chemical Society*.

In the examples that follow: "mg" means milligram(s), "M" means molar, "mL" means milliliter(s), "mmol" means millimole(s), "L" means liter(s), "mol" means mole(s), "g" means gram(s), "TLC" means thin layer chromatography, "HPLC" means high pressure liquid chromatography, "mm" means millimole(s), "mp" means melting point, "Mhz" means Megaherz, "$^1$H-NMR" means proton nuclear magnetic resonance, "Hz" means Hertz, "h" means hour(s) and "n" means normal.

Unless otherwise noted all starting materials were obtained from commercial suppliers and used without further purification. All reactions involving oxygen or moisture-sensitive compounds were performed under a dry $N_2$ atmosphere. All reactions and chromatography fractions were analyzed by thin-layer chromatography on silica gel plates, visualized with UV light and $I_2$ stain.

Example 1

4-Ethyl-1H-pyrano[3,4-c]pyridin-8-one

A compound of Formula (VI) wherein $R_5$ is hydrogen and $R_6$ is methyl

A 250-mL one-neck round-bottom flask is charged with 4-ethyl-8-methoxy-1H-pyrano[3,4-c]pyridine (10 g, 52.4 mmol), prepared as described in U.S. patent application Ser. No. 08/237,081, Fang et al., Journal of Organic Chemistry, 59(21), 6142–6143 (1994), PCT/US95/05425 and PCT/US95/05427, acetonitrile (100 mL), and sodium iodide (11.8 g, 79 mmol). This mixture is stirred for about 20 minutes at ambient temperature. To the mixture is added trimethylsilylchloride (10 mL, 79 mmol) causing the immediate formation of a white precipitate. The resulting mixture is heated at reflux for about 2 hours. The reaction is cooled to ambient temperature. To the cooled reaction mixture is added 50 mL of saturated sodium bicarbonate solution. The mixture is stirred for 1 hour at ambient temperature. The precipitate is collected by filtration on a buchner funnel. The collected solid is dried in vacuo for about 12 hours at between 25 and 38° C. to provide a first crop 4-ethyl-1H-pyrano[3,4-c]pyridin-8-one as a slightly tan crystalline solid. The filtrate is concentrated in vacuo and the resulting residue recrystallized from acetonitrile/methanol to give additional 4-ethyl-1H-pyrano[3,4-c]pyridin-8-one as a slightly tan crystalline solid. Characterization data: mp 169–171° C. $^1$H NMR (CDCl$_3$, 300 MHz): δ 1.11 (t, J=7.4 Hz, 3H), 2.27 (q, J=7.4 Hz, 2H), 5.04 (s, 2H), 6.17 (d, J=6.8 Hz, 1H), 6.59 (s, 1H), 7.32 (d, J=6.8 Hz, 1H), 13.16 (bs, 1H).

Example 2

4-Ethyl-7-[7-iodo-9-[(4-methyl-piperazinyl)methyl]-2,3-dihydro-[1,4]dioxino[2,3-g]quinolin-8-ylmethyl]-1H -pyrano[(3,4-c]pyridin-8-one A compound of Formula (IV) wherein $R_1$ is 4-methylpiperazinyl-methyl, $R_2$, is hydrogen, $R_3$ and $R_4$ together are ethylenedioxy, $R_5$ is hydrogen, $R_6$ is methyl, and X is iodo To a solution of 4-ethyl-1H-pyrano[3,4-c]pyridin-8-one (200 mg, 1.13 mmol) and [7-iodo-9-[(4-methyl-piperazinyl)methyl]-2,3-dihydro-[1,4]dioxino[2,3-g]quinolin-8-yl]-methanol (514 mg,1.13 mmol), prepared as described in U.S. patent application Ser. No. 08/237,081, Fang et al., Journal of Organic Chemistry, 59(21), 6142–6143(1994), PCT/US95/05425, and PCT/US95/05427, in 4.5 mL of dichloromethane is added triphenylphosphine (326 mg, 1.24 mmol). After being stirred at ambient temperature for 3 min, the mixture is cooled to 0° C., followed by dropwise addition of diethyl azodicarboxylate (0.20 mL, 1.24 mmol). The brown solution is warmed to ambient temperature and stirred for 14 h. The solvent is removed under reduced pressure and the resultant residue is chromatographed on silica gel. Elution with 5–10% methanol in dichloromethane affords 4-ethyl-7-[7-iodo-9-[(4-methyl-piperazinyl)methyl]-2,3-dihydro-[1,4]dioxino[2,3-g]quinolin-8-ylmethyl]-1H-pyrano[3,4-c]pyridin-8-one as a yellow solid. Characterization data: $^1$H NMR (200 MHz, CDCl3): δ 1.03 (t, J=7.4 Hz, 3H), 2.18 (s, 3H), 2.25 (q, J=7.4 Hz, 2H), 2.45 (br. s, 4H), 3.80 (s, 2H), 4.39 (s, 4H), 5.18 (s, 2H), 5.45 (s, 2H), 5.94 (d, J=6.8 Hz, 1H), 6.60 (s, 1H), 6.80 (d, J=6.8 Hz, 1H), 7.52 (s, 1H), 7.67 (s, 1H).

Example 3

11H-1,4-Dioxino[2,3-g]pyrano[3'4':6,7]indolizino[1,2-b]quinoline-12(14H)-one,8-ethyl-2,3-dihydro-15-[(4-methyl-1-piperazinyl)methyl]

A compound of Formula (II) wherein $R_1$ is 4-methylpiperazinyl-methyl, $R_2$ is hydrogen, $R_3$ and $R_4$ together are ethylenedioxy, $R_5$ is hydrogen, and $R_6$ is methyl To a solution of 4-ethyl-7-[7-iodo-9-[(4-methyl-piperazinyl)methyl]-2,3-dihydro-[1,4]dioxino[2,3-g]quinolin-8-ylmethyl]-1H-pyrano[3,4-c]pyridin-8-one (50.0 mg, 0.0813 mmol) in 4 mL of acetonitrile is successively added palladium(II) acetate (0.90 mg, 0.0040 mmol), powdered anhydrous potassium carbonate (22.4 mg, 0.163 mmol) and triphenylphosphine (10.6 mg, 0.0406 mmol) at ambient temperature. The mixture is brought to reflux and stirred for 17 h. The solvent is removed under reduced pressure and the resultant residue is chromatographed on silica gel. Elution with 10% methanol in chloroform yields 11H-1,4-Dioxino[2,3-g]pyrano[3'4':6,7]indolizino[1,2-b]quinoline-12(14H)-one,8-ethyl-2,3-dihydro-15-[(4-methyl-1-piperazinyl)methyl] as a yellow solid: Characterization data: mp 223–225° C. $^1$H NMR (300 MHz, CDCl3): δ 1.22 (t, J=7.4 Hz, 3H), 2.29 (s, 3H), 2.45 (q, J=7.4 Hz, 2H), 2.57 (br. s, 4H), 3.94 (s, 2H), 4.44 (s, 4H), 5.20 (s, 2H), 4.83 (s, 1H), 5.29 (s, 2H), 6.67 (s, 2H), 7.14 (s, 1H), 7.65 (s, 1H), 7.75 (s, 1H).

Example 4

11H-1,4-Dioxino[2,3-g]pyrano[3',4':6,7]indolizino [1,2-b]quinoline-12(8H,14H)-one,8-ethyl-2,3-dihydro-8,9-dihydroxy-15-[(4-methyl-1-piperazinyl) methyl]-(9R-cis)

A compound of Formula (III) wherein $R_1$ is 4-methylpiperazinyl-methyl, $R_2$ is hydrogen, $R_3$ and $R_4$ together are ethylenedioxy, $R_5$ is hydrogen, and $R_6$ is methyl).

To AD-mix-β (1.26 g), containing the chiral ligand hydroquinidine 1,4-phthalazinediyl diether, available from Aldrich Chemical Company, Milwaukee, Wis., in 4 mL of water-tert-butyl alcohol (1:1) is added methanesulfonamide (24 mg, 0.260 mmol). The brown mixture is cooled to 0 ° C., followed by addition of 11H-1,4-Dioxino[2,3-g]pyrano[3'4':6,7]indolizino[1,2-b]quinoline-12(14H)-one,8-ethyl-2,3-dihydro-15-[(4-methyl-1-piperazinyl)methyl] (126 mg, 0.260 mmol). The mixture is allowed to warm to ambient temperature and vigorously stirred for 36 h. The mixture is diluted with 8 mL of water and quenched with 750 mg of sodium sulfite. After being stirred for an additional 20 min, the mixture is diluted with 5 mL of dichloromethane and filtered to give a solid which is dried in high vaccum to provide 11H-1,4-Dioxino[2,3-g]pyrano[3',4':6,7]indolizino [1,2-b]quinoline-12(8H,14H)-one,8-ethyl-2,3-dihydro-8,9-dihydroxy-15-[(4-methyl-1-piperazinyl)methyl]-(9R-cis) as a light yellow solid. $^1$H NMR indicates a diastereomeric ratio of 83:17. Presumably, the two diastereomers are epimeric in the hemiacetal carbon. Characterization data (major epimer): mp 255–260° C. with decomposition. $^1$H NMR (300 MH, DMSO-d6): δ 0.97 (t, J=7.4 Hz, 3H), 1.74 (q, J=7.4 Hz, 2H), 2.06 (s, 3H), 2.29 (br. s, 4H), 3.89 (s, 2H), 4.39 (s, 4H), 4.51 (ABq, $J_{AB}$=39 Hz, Δv=82 Hz, 2H), 4.83 (s, 1H), 4.95 (s, 1H), 5.26 (s, 2H), 7.23 (s, 1H), 7.54 (s, 1H), 7.70 (s, 1H).

In order to assess the enantiomeric selectivity of the above process, the major diastereomer above is separately converted to the (S)- and (R)-O-methylmandelates by the following protocol. A mixture of the above solid (10 mg, 0.019 mmol), (S)-O-methylmandelic acid (6.4 mg, 0.038 mmol), 1,3-dicyclohexylcarbodiimide (7.9 mg, 0.038 mmol) and a catalytic amount of N,N-dimethylaminopyridine in 2 mL of dichloromethane is stirred at ambient temperature for 2 h. The resulting white suspension is filtered through a short pad of Celite® and washed with 2 mL of dichloromethane. The combined filtrate and washings are concentrated under reduced pressure to yield a crude product as a solid. Analysis on the integrals of the $^1$H NMR spectrum (300 MHz, CDCl$_3$) indicates a diastereomeric ratio of 93:7. This corresponds to 86% enantiopurity for the major pentacyclic alcohol. The same ratio is obtained when (R)-mandelates are prepared from the major alcohol. The signals for the (S)- and (R)-O-methylmandelates are complementary to each other. In both cases, the sharp signal for the proton of the anomeric center is used for analysis.

Example 5

11H-1,4-Dioxino[2,3-g]pyrano[3',4':6,7]indolizino [1,2-b]quinoline-9,12(8H,14H)-dione,8-ethyl-2,3-dihydro-8-hydroxy-15-[(4-methyl-1-piperazinyl) methyl]-(S)

A compound of Formula (I) wherein $R_1$ is 4-methylpiperazinyl-methyl, $R_2$ is hydrogen, $R_3$ and $R_4$ together are ethylenedioxy, $R_5$ is hydrogen, and $R_6$ is methyl A solution of oxalyl chloride (0.14 mL, 1.5 mmol) in 8 mL of dichloromethane is cooled to −78° C., followed by dropwise addition of dimethyl sulfoxide (0.22 mL, 3.1 mmol). The mixture is stirred for 2 min, and then 11H-1,4-Dioxino[2,3-g]pyrano[3',4':6,7]indolizino[1,2-b]quinoline-12(8H,14H)-one,8-ethyl-2,3-dihydro-8,9-dihydroxy-15[(4-methyl-1-piperazinyl)methyl]-(9R-cis) (40 mg, 0.077 mmol) is added in dimethyl sulfoxide (2 mL). After being stirred at −78° C. for 15 min, the mixture is treated with triethylamine (0.85 mL, 6.2 mmol) dropwise. The cooling bath is removed and the stirring is continued for 10 min. After being quenched with 10 mL of water, the layers are separated and the aqueous layer is extracted with chloroform three times. The combined organic layers are washed with saturated aqueous sodium chloride, dried over anhydrous sodium sulfate and concentrated under reduced pressure. The resultant brown residue is chromatographed on silica gel. Elution with 10% methanol in chloroform provides 26 mg (65% yield) of 11H-1,4-Dioxino[2,3-g]pyrano[3',4':6,7] indolizino[1,2-b]quinoline-9,12(8H,14H)-dione,8-ethyl-2, 3-dihydro-8-hydroxy-15-[(4-methyl-1-piperazinyl)methyl]-(S) as a yellow solid. Characterization data: $^1$H NMR (300 MH, CDCl3): δ 1.06 (t, J=7.4 Hz, 3H), 1.91 (m, 2H), 2.31 (s, 3H), 2.59 (br. s, 4H), 3.80 (br. s, 1H), 3.97 (s, 2H), 4.46 (s, 4H), 5.32 (s, 2H), 5.55 (ABq, $J_{AB}$=8.4 Hz, Δv=90 Hz, 2H), 7.60 (s, 1H), 7.66 (s, 1H), 7.72 (s, 1H).

We claim:

1. A method of preparing a compound of Formula (I),

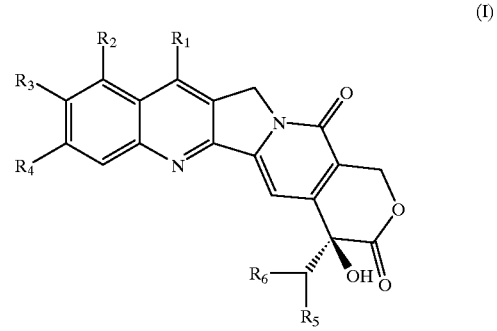

(I)

which comprises dihydroxylating a compound of Formula (II),

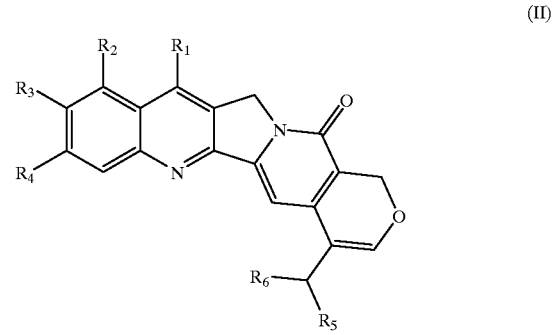

(II)

wherein:

$R_1$ and $R_2$, which may be the same or different, are independently selected from hydrogen, lower alkyl, ($C_{3-7}$) cycloalkyl, ($C_{3-7}$)cycloalkyl lower alkyl, lower alkenyl, hydroxy lower alkyl, or alkoxy alkyl, or (—CH$_2$NR$_7$R$_8$), wherein:
i) $R_7$ and $R_8$, which may be the same or different, are independently selected from hydrogen, lower alkyl, ($C_{3-7}$) cycloalkyl, ($C_{3-7}$) cycloalkyl lower alkyl, lower alkenyl, hydroxy lower alkyl, or lower alkoxy lower alkyl; or
ii) $R_7$ represents hydrogen, lower alkyl, ($C_{3-7}$) cycloalkyl, ($C_{3-7}$) cycloalkyl lower alkyl, lower alkenyl, hydroxy lower alkyl, or lower alkoxy lower alkyl, and $R_8$ represents —COR$_9$, wherein:
$R_9$ represents hydrogen, lower alkyl, perhalo-lower alkyl, ($C_{3-7}$)cycloalkyl, ($C_{3-7}$) cycloalkyl lower alkyl, lower alkenyl, hydroxy lower alkyl, lower alkoxy, lower alkoxy lower alkyl; or
iii) $R_7$ represents hydrogen or lower alkyl; and $R_8$ represents diphenyl-methyl or —(CH$_2$)$_t$Ar wherein:
t is 0 to 5 and Ar represents phenyl, furyl, pyridyl, N-methylpyrrolyl, imidazolyl optionally substituted with one or more substituents selected from hydroxy, methyl, halogen, and amino; or iv) $R_7$ and $R_8$ taken together with the linking nitrogen form a saturated 3 to 7 atom heterocyclic group of formula (IA)

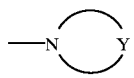
(IA)

wherein:

Y represents O, S, SO, $SO_2$, $CH_2$ or $NR_{10}$, wherein:

$R_{10}$ represents hydrogen, lower alkyl, perhalo lower alkyl, aryl, aryl substituted with one or more substituents selected from lower alkyl, lower alkoxy, halogen, nitro, amino, lower alkyl amino, perhalo-lower alkyl, hydroxy lower alkyl, lower alkoxy lower alkyl groups or —$COR_{11}$, wherein:

$R_{11}$ represents hydrogen, lower alkyl, perhalo-lower alkyl, lower alkoxy, aryl, aryl substituted with one or more substituents selected from lower alkyl, perhalo-lower alkyl, hydroxy lower alkyl, lower alkoxy lower alkyl groups; and $R_3$ and $R_4$ are independently selected from hydrogen, loyr alkyl, $(C_{3-7})$cycloalkyl, $(C_{3-7})$cycloalkyl lower alkyl, lower alkenyl, hydroxy lower alkyl, or alkoxy alkyl; or $R_3$ and $R_4$ taken together form a saturated 5 to 6 atom heterocyclic group of formula (IB)

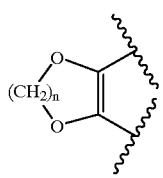
(IB)

wherein, n represents the integer 1 or 2; or $R_3$ represents —$OCONR_{12}R_{13}$, wherein, $R_{12}$ and $R_{13}$, which may be the same or different, are independently selected from hydrogen, a substituted or unsubstituted alkyl group with 1–4 carbon atoms or a substituted or unsubstituted carbocyclic or heterocyclic group, with the proviso that when both $R_{12}$ and $R_{13}$ are substituted or unsubstituted alkyl groups, they may be combined together with the nitrogen atom, to which they are bonded, to form a heterocyclic ring which may be interrupted with —O—, —S— and/or >N—$R_{14}$ in which $R_{14}$ is hydrogen, a substituted or unsubstituted alkyl group with 1–4 carbon atoms or a substituted or unsubstituted phenyl group, and $R_5$ represents hydrogen or alkyl, and $R_6$ represents hydrogen or alkyl, and pharmaceutically acceptable salts thereof.

2. A compound of Formulas (II), or (III):

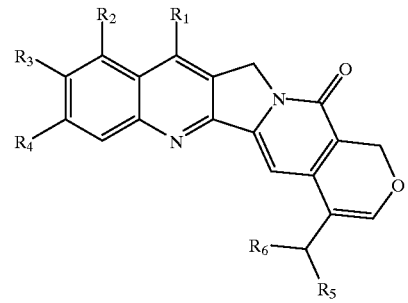
(II)

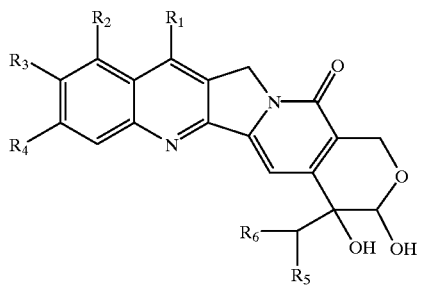
(III)

wherein:

$R_1$ is (—$CH_2NR_7R_8$) and $R_2$ is selected from hydrogen, lower alkyl, $(C_{3-7})$ cycloalkyl, $(C_{3-7})$cycloalkyl lower alkyl, lower alkenyl, hydroxy lower alkyl, or alkoxy alkyl, or (—$CH_2NR_7R_8$), wherein:

i) $R_7$ and $R_8$, which may be the same or different, are independently selected from hydrogen, lower alkyl, $(C_{3-7})$ cycloalkyl, $(C_{3-7})$ cycloalkyl lower alkyl, lower alkenyl, hydroxy lower alkyl, or lower alkoxy lower alkyl; or ii) $R_7$ represents hydrogen, lower alkyl, $(C_{3-7})$ cycloalkyl, $(C_{3-7})$ cycloalkyl lower alkyl, lower alkenyl, hydroxy lower alkyl, or lower alkoxy lower alkyl, and $R_8$ represents —$COR_9$, wherein:

$R_9$ represents hydrogen, lower alkyl, perhalo-lower alkyl, $(C_{3-7})$cycloalkyl, $(C_{3-7})$ cycloalkyl lower alkyl, lower alkenyl, hydroxy lower alkyl, lower alkoxy, lower alkoxy lower alkyl; or iii) $R_7$ represents hydrogen or lower alkyl; and $R_8$ represents diphenyl-methyl or —$(CH_2)_tAR$ wherein:

t is 0 to 5 and Ar represents phenyl, furyl, pyridyl, N-methylpyrrolyl, imidazolyl optionally substituted with one or more substituents selected from hydroxy, methyl, halogen, and amino; or iv) $R_7$ and $R_8$ taken together with the linking nitrogen form a saturated 3 to 7 atom heterocyclic group of formula (IA)

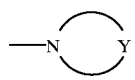

(IA)

wherein:

Y represents O, S, SO, $SO_2$, $CH_2$ or $NR_{10}$, wherein:

$R_{10}$ represents hydrogen, lower alkyl, perhalo lower alkyl, aryl, aryl substituted with one or more substituents selected from lower alkyl, lower alkoxy, halogen, nitro, amino, lower alkyl amino, perhalo-lower alkyl, hydroxy lower alkyl, lower alkoxy lower alkyl groups or —$COR_{11}$, wherein:

$R_{11}$ represents hydrogen, lower alkyl, perhalo-lower alkyl, lower alkoxy, aryl, aryl substituted with one or more substituents selected from lower alkyl, perhalo-lower alkyl, hydroxy lower alkyl, lower alkoxy lower alkyl groups; and $R_3$ and $R_4$ are independently selected from hydrogen, lower alkyl, ($C_{3-7}$)cycloalkyl, ($C_{3-7}$)cycloalkyl lower alkyl, lower alkenyl, hydroxy lower alkyl, or alkoxy alkyl; or $R_3$ and $R_4$ taken together form a saturated 5 to 6 atom heterocyclic group of formula (IB)

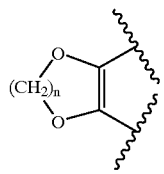

(IB)

wherein, n represents the integer 1 or 2; or $R_3$ represents —$OCONR_{12}R_{13}$, wherein, $R_{12}$ and $R_{13}$, which may be the same or different, are independently selected from hydrogen, a substituted or unsubstituted alkyl group with 1–4 carbon atoms or a substituted or unsubstituted carbocyclic or heterocyclic group, with the proviso that when both $R_{12}$ and $R_{13}$ are substituted or unsubstituted alkyl groups, they may be combined together with the nitrogen atom, to which they are bonded, to form a heterocyclic ring which may be interrupted with —O—, —S— and/or >N—$R_{14}$ in which $R_{14}$ is hydrogen, a substituted or unsubstituted alkyl group with 1–4 carbon atoms or a substituted or unsubstituted phenyl group, and $R_5$ represents hydrogen or alkyl, and $R_6$ represents hydrogen or alkyl, and pharmaceutically acceptable salts thereof.

3. A compound selected from the group consisting of:
11H-1,4-Dioxino[2,3g]pyrano[3',4':6,7]indolizino[1,2-b]quinoline-12(14H)-one, 8-ethyl-2,3-dihydro-15-[(4-methyl-1-piperazinyl)methyl]; or
11H-1,4-Dioxino[2,3-g]pyrano[3',4':6,7]indolizino[1,2-b]quinoline-12(8H, 14H)-one,8-ethyl-2,3-dihydro-8,9-dihydroxy-15-[(4-methyl-1-piperazinyl)methyl]-(9R-cis).

4. The method of claim 1, wherein dihydroxylation of the compound of formula II results in a compound of formula III which is subsequently oxidized to the compound of formula I,

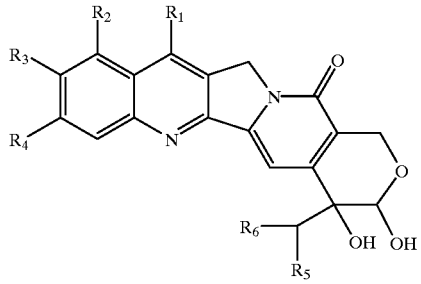

(III)

wherein:

$R_1$ and $R_2$, which may be the same or different, are independently selected from hydrogen, lower alkyl, ($C_{3-7}$) cycloalkyl, ($C_{3-7}$)cycloalkyl lower alkyl, lower alkenyl, hydroxy lower alkyl, or alkoxy alkyl, or (—$CH_2NR_7R_8$), wherein:

i) $R_7$ and $R_8$, which may be the same or different, are independently selected from hydrogen, lower alkyl, ($C_{3-7}$) cycloalkyl, ($C_{3-7}$) cycloalkyl lower alkyl, lower alkenyl, hydroxy lower alkyl, or lower alkoxy lower alkyl; or ii) $R_7$ represents hydrogen, lower alkyl, ($C_{3-7}$) cycloalkyl, ($C_{3-7}$) cycloalkyl lower alkyl, lower alkenyl, hydroxy lower alkyl, or lower alkoxy lower alkyl, and $R_8$ represents —$COR_9$, wherein:

$R_9$ represents hydrogen, lower alkyl, perhalo-lower alkyl, ($C_{3-7}$)cycloalkyl, ($C_{3-7}$) cycloalkyl lower alkyl, lower alkenyl, hydroxy lower alkyl, lower alkoxy, lower alkoxy lower alkyl; or iii) $R_7$ represents hydrogen or lower alkyl; and $R_8$ represents diphenyl-methyl or —$(CH_2)_t Ar$ wherein:

t is 0 to 5 and Ar represents phenyl, furyl, pyridyl, N-methylpyrrolyl, imidazolyl optionally substituted with one or more substituents selected from hydroxy, methyl, halogen, and amino; or iv) $R_7$ and $R_8$ taken together with the linking nitrogen form a saturated 3 to 7 atom heterocyclic group of formula (IA)

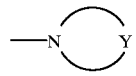

(IA)

wherein:

Y represents O, S, SO, $SO_2$, $CH_2$ or $NR_{10}$, wherein:

$R_{10}$ represents hydrogen, lower alkyl, perhalo lower alkyl, aryl, aryl substituted with one or more substituents selected from lower alkyl, lower alkoxy, halogen, nitro, amino, lower alkyl amino, perhalo-lower alkyl, hydroxy lower alkyl, lower alkoxy lower alkyl groups or —$COR_{11}$, wherein:

$R_{11}$ represents hydrogen, lower alkyl, perhalo-lower alkyl, lower alkoxy, aryl, aryl substituted with one or more substituents selected from lower alkyl, perhalo-lower alkyl, hydroxy lower alkyl, lower alkoxy lower alkyl groups; and $R_3$ and $R_4$ are independently selected from hydrogen, lower alkyl, ($C_{3-7}$)cycloalkyl, ($C_{3-7}$)cycloalkyl lower alkyl, lower alkenyl, hydroxy lower alkyl, or alkoxy alkyl; or $R_3$ and $R_4$ taken together form a saturated 5 to 6 atom heterocyclic group of formula (IB)

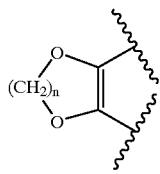

(IB)

wherein, n represents the integer 1 or 2; or $R_3$ represents —OCONR$_{12}$R$_{13}$, wherein, $R_{12}$ and $R_{13}$, which may be the same or different, are independently selected from hydrogen, a substituted or unsubstituted alkyl group with 1–4 carbon atoms or a substituted or unsubstituted carbocyclic or heterocyclic group, with the proviso that when both $R_{12}$ and $R_{13}$ are substituted or unsubstituted alkyl groups, they may be combined together with the nitrogen atom, to which they are bonded, to form a heterocyclic ring which may be interrupted with —O—, —S— and/or >N—R$_{14}$ in which R$_{14}$ is hydrogen, a substituted or unsubstituted alkyl group with 1–4 carbon atoms or a substituted or unsubstituted phenyl group, and $R_5$ represents hydrogen or alkyl, and $R_6$ represents hydrogen or alkyl, and pharmaceutically acceptable salts thereof.

5. The method of claim 1, wherein the compound of formula II is 11H-1,4-Dioxino[2,3-g]pyrano[3',4':6,7]indolizino[1,2-b]quinoline-12(14H)-one,8-ethyl-2,3-dihydro-15-[(4-methyl-1-piperazinyl)methyl].

6. The method of claim 4, wherein the compound of formula III is 11H-1,4-Dioxino[2,3-g]pyrano[3',4':6,7]indolizino[1,2b]quinoline-12(8H,14H)-one,8-ethyl-2,3-dihydro-8,9-dihydroxy-15-[(4-methyl-1-piperazinyl)methyl]-(9R-cis).

7. The compound of claim 2, wherein the compound is 11H-1,4-Dioxino[2,3-g]pyrano[3',4':6,7]indolizino[1,2b]quinoline-12(14H)-one,8-ethyl-2,3-dihydro-15-[(4-methyl-1-piperazinyl)methyl].

8. The compound of claim 2, wherein the compound is 11H-1,4-Dioxino[2,3-g]pyrano[3',4':6,7]indolizino[1,2-b]quinoline-12(8H,14H)-one,8-ethyl-2,3-dihydro-8,9-dihydroxy-15-[(4-methyl-1-piperazinyl)methyl]-(9R-cis).

* * * * *